United States Patent
Tanimura et al.

[11] Patent Number: 6,103,190
[45] Date of Patent: *Aug. 15, 2000

[54] MICROORGANISM MULTIPLICATION PREVENTING METHOD AND APPARATUS

[75] Inventors: Yasuhiro Tanimura; Koji Ota; Takesi Sugimoto; Masao Kawasaki; Daisyuu Hirayama, all of Tokyo, Japan

[73] Assignee: Mitsubishi Denki Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/732,576

[22] Filed: Oct. 15, 1996

[30] Foreign Application Priority Data

Oct. 24, 1995 [JP] Japan ................... 7-275625

[51] Int. Cl.$^7$ ........................................... A61L 2/20
[52] U.S. Cl. .................... 422/29; 422/3; 422/22; 422/305
[58] Field of Search ............... 422/120, 30, 122, 422/69, 88, 177, 211, 312, 22, 29, 3, 305

[56] References Cited

U.S. PATENT DOCUMENTS

| | | | |
|---|---|---|---|
| 4,390,461 | 6/1983 | Tsukiyama et al. | 252/519 |
| 5,010,869 | 4/1991 | Lee | 123/539 |
| 5,445,798 | 8/1995 | Ikeda et al. | 422/121 |
| 5,484,570 | 1/1996 | Ikeda et al. | 422/1 |
| 5,527,459 | 6/1996 | Ikeda et al. | 210/188 |
| 5,591,349 | 1/1997 | Ikeda et al. | 210/760 |
| 5,648,046 | 7/1997 | Weibel | 422/4 |

FOREIGN PATENT DOCUMENTS

| | | |
|---|---|---|
| 60-063459 | 11/1985 | Japan . |
| 7-115946 | of 1995 | Japan . |
| 392945 | 8/1931 | United Kingdom . |
| 2273048A | 6/1994 | United Kingdom . |
| 93-22603 | 11/1993 | WIPO . |

OTHER PUBLICATIONS

Kuffler et al., From Neuron to Brain, Sinauer Associates Inc.: Sunderland, MA, p. 288, 1984.

*Primary Examiner*—Elizabeth McKane
*Attorney, Agent, or Firm*—Sughrue, Mion, Zinn, Macpeak & Seas, PLLC

[57] ABSTRACT

A method for preventing microorganism multiplication, including using a gas containing a low concentration of ozone and a high concentration of ions, so that the multiplication of microorganisms can be safely and fully prevented by an additive effect of the ozone and ions. The generation of ozone is suppressed by reducing the discharge current in the ionization chamber using a pulse converter, which is provided to control the current flowing at the time of discharge, when generating the ions and ozone in the ionization chamber. Ions are produced in the ionization chamber in a high concentration to produce and supply ionized gas containing a low concentration of ozone and a high concentration of ions, which prevents microorganism multiplication on the objects.

10 Claims, 14 Drawing Sheets

MICROORGANISM MULTIPLICATION PREVENTING METHOD AND APPARATUS

BACKGROUND OF THE INVENTION

1. Field of the Invention

The present invention relates to a microorganism multiplication preventing method and apparatus for preventing the multiplication of microorganisms existing on the surface of objects in which the multiplication preventing of microorganisms is needed from the viewpoint of public health, such as foods, cooking utensils and other required tools related to foods, and for preventing the multiplication of microorganisms existing in a space for housing these objects' by using activated particles such as ions or ozone.

2. Description of Related Art

FIG. 14 is a structural drawing showing the microorganism multiplication preventing apparatus disclosed in Japanese Patent Laid-Open No. 7-115946. In FIG. 14, numerals 1 denote outdoor gas, the apparatus comprises a fan (ventilator) 2 for drawing the gas 1, a vent passage 3 for allowing the gas 1 drawn by the fan 2 to flow and a supply port 4 provided on the outdoor side of the fan 2 for drawing the gas 1. Further the apparatus comprises an ionization chamber 5 provided in the vent passage 3 for ionizing the drawn gas 1 by electrically detaching electrons, a bushing 6 provided in the vent passage 3 and made of insulating materials, metal needle electrodes 7 protruding into the passage duct 3 and made of metallic material such as tungsten, stainless steel or nickel, a metal plate 8 ground electrode placed in the vent passage 3 opposite the metal needle electrodes 7, and a plate dielectric 9 made of dielectric material, attached onto the metal plate ground electrode 8 by vapor deposition or close adhesion, such as ceramic, glass or quartz. Ionized gas containing ozone, ionized in the ionization chamber and flows through the vent passage 3 and an ozone decomposition chamber 11 filled with an ozone dissociating catalyzer, such as manganese dioxide or activated alumina, for decomposing the ozone contained in the ozone-contained gas 10 having been ionized in the ionization chamber 5. The ozone decomposition chamber 11 removes the ozone from the ozone-contained ionized gas 10. Furthermore, numeral 14 denotes objects placed in the ion treatment chamber, mentioned later, on which microoganisms multiply, the apparatus comprising an insulator 12 for electrically insulating the ozone decomposing chamber 11 from the vent passage 3, the ozone-free ionized gas 13 being sent from the vent passage 3 in the ion treatment chamber 15, mentioned later, the ion treatment chamber 15 having space enough for housing the objects for microorganisms to multiply thereon, to which the ozone-free ionized gas 13 is supplied after removal of ozone in the ozone decomposition chamber 11. The apparatus further comprises a high-voltage generator 16 for applying a high voltage between the metal needle electrodes 7 and the metal plate ground electrode 8, a gas inlet 17 for supplying the ozone-free ionized gas 13 to the ion treatment chamber 15 and a gas outlet 18 for releasing the used ozone-free ionized gas 13 to outside the ion treatment chamber 15, respectively.

Next, the operation will be described.

First, outdoor gas 1 is drawn from the supply port 4 by the fan 2 and led through the vent passage 3 into the ionization chamber 5.

In this ionization chamber 5, a plurality of metal needle electrodes 7 and a metal plate ground electrode 8 attached by close adhesion to the dielectric 9 placed opposite the metal needle electrodes 7, are disposed with a space (gap length) between both electrodes 7, 8 set at several millimeters. On application of an AC high voltage of several kV between both electrodes 7, 8, a high electric field is generated near the top of metal needle electrodes 7 and an electric discharge, known as a corona discharge, takes place.

When the gas 1 is led into the ionization chamber 5, oxygen molecules and other particles contained in the gas 1 collide with electrons so that oxygen molecules and other particles are ionized and consequently ions are contained in the gas 1.

However, since oxygen molecules are contained in the outdoor gas 1, ozone is also generated at the same time when ions are generated. Incidentally, because of its high oxidation power, this ozone is harmful if its concentration becomes high.

Accordingly, downstream in the vent passage 3, an ozone dissociation catalyzer, electrically insulated from the vent passage 3, is placed in the ozone dissociation chamber 11 and ozone is removed from the ozone-contained ionized gas 10 by using this ozone dissociation catalyzer to produce a ozone-free ionized gas 13.

The ozone-free ionized gas 13 produced in this manner is supplied to the ion treatment chamber 15 having a space for housing objects 14 for microorganisms to multiply thereon, to prevent the microorganisms stuck on the objects 14 from multiplying.

A conventional microorganism multiplication preventing apparatus is thus arranged and the ions generated in this apparatus are effective to prevent the multiplication of microorganisms. However, the generation amount of ions is limited and the self dissociation of ions increases with higher ion concentration in the gas, so that there is a problem that a high concentration of ions cannot be sufficiently supplied to the microorganisms stuck on the object. Another problem is that when the ion treatment stops, the multiplication starts again because only the ions are used. Therefore satisfactory effects on the prevention of microorganism multiplication are not obtained.

On the other hand, if ozone is used to prevent the multiplication of microorganisms, treatment with an ozone concentration of 0.1 ppm or higher is required, but in the region of concentration of 0.1 ppm or higher, the high oxidization power of the ozone causes a problem that, for example, some foods are discolored/denatured or equipment parts corrode.

SUMMARY OF THE INVENTION

Object of the Invention

As a result of intensive investigation for solving the above problems, the present invention is made by finding that a low concentration of ozone is allowed to be contained in the gas containing ions for preventing the multiplication of microorganisms and the preventive capacity against microorganism multiplication can be elevated due to the additive effects of ozone and ions.

It is one object of the present invention to obtain a microorganism multiplication preventing apparatus with a high preventive capacity against microorganism multiplication capable of sufficiently suppressing the multiplication of microorganisms with safety and the like, in treatment.

It is another object of the present invention to obtain a microorganism multiplication preventing apparatus with a high preventive capacity against microorganism multiplication capable of generating ions at a high concentration and controlling ozone at a low concentration by suppressing the generation of ozone as well.

It is a third object of the present invention to obtain a microorganism multiplication preventing apparatus with a high preventive capacity against microorganism multiplication capable of generating ions efficiently and at a high concentration in the gases while controlling the generation of ozone to a low concentration.

It is a fourth object of the present invention to obtain a microorganism multiplication preventing apparatus capable of easily controlling the ozone concentration and not only generating ions continuously and at a high concentration, but also sensing the life of activated-particle generating electrodes.

Summary of the Invention

A first microorganism multiplication preventing method according to the present invention is so arranged as to suppress the ozone generation and generate a gas containing a predetermined concentration of ozone and a high concentration of ions in ionizing and ozonizing gas under action of a discharge, thereby preventing the multiplication of microorganisms, for example, stuck on objects or floating in space.

A second microorganism multiplication preventing method according to the present invention is so arranged as to suppress the ozone generation and generate a gas containing a predetermined concentration of ozone and a high concentration of ions in ionizing and ozonizing gas under action of a discharge, then spraying this gas, for example, on objects where microorganisms multiply thereon. With this arrangement, the preventive capacity against microorganism multiplication can be elevated due to the additive effects of ozone and ions and moreover the multiplication of microorganisms can be prevented fully without reducing the safety and the like during treatment.

A first microorganism multiplication preventing apparatus according to the present invention is provided with discharge current control means for controlling the current flowing at a discharge for generating ions and ozone in an activated-particle generating chamber to regulate the ozone concentration in the gas to a low concentration.

In addition, the discharge current control means is so arranged as to comprise a pulse generator. With this arrangement, the discharge current can be reduced, the generation of ozone can be suppressed while allowing ions to be generated and the concentration of ozone can be regulated to a low value. That is, a predetermined low concentration of ozone can be constantly generated in a gas containing a high concentration of ions, so that the preventive capacity against microorganism multiplication can be elevated due to the additive effects of ozone and ion and moreover the multiplication of microorganisms can be prevented fully without reducing the safety and the like during treatment.

Furthermore, in addition to the above-mentioned, discharge current control means for measuring the current flowing at the time of discharge is provided. With this arrangement, a value of current used in the activated-particle electrodes can be detected, the concentration of ozone can be easily controlled to a low concentration and the multiplication of microorganisms can be prevented safely and efficiently.

A second microorganism multiplication preventing apparatus according to the present invention has gas flow control means provided on the upstream side of the activated-particle generating chamber for leading the gas to near the discharge electrode of the activated-particle generating electrodes or into the gap between the electrodes, and moreover, regulating the flow speed of the gas. With this arrangement, the generation of ions can be increased without an increase in the generation of ozone by accelerating the speed of gas between the electrodes and accordingly gas containing a predetermined low concentration of ozone and a high concentration of ions can be generated, so that the preventive capacity against microorganism multiplication can be elevated due to an additive effect of ozone and ions and moreover the multiplication of microorganisms can be prevented fully without injury and the like during treatment.

In addition to the above-mentioned, a third microorganism multiplication preventing apparatus further comprises ozone concentration regulating means for regulating the ozone concentration in the gas taken into the activated-particle generating chamber. With this arrangement, the ozone concentration of the gas containing ozone and ions supplied becomes easy to control, ozone can be maintained to a low concentration and the multiplication of microorganisms can be prevented safely and efficiently.

DETAILED DESCRIPTION OF THE PREFERRED EMBODIMENTS

Embodiment 1

Hereinafter, embodiments of the present invention will be described with reference to the drawings.

Figure 1:
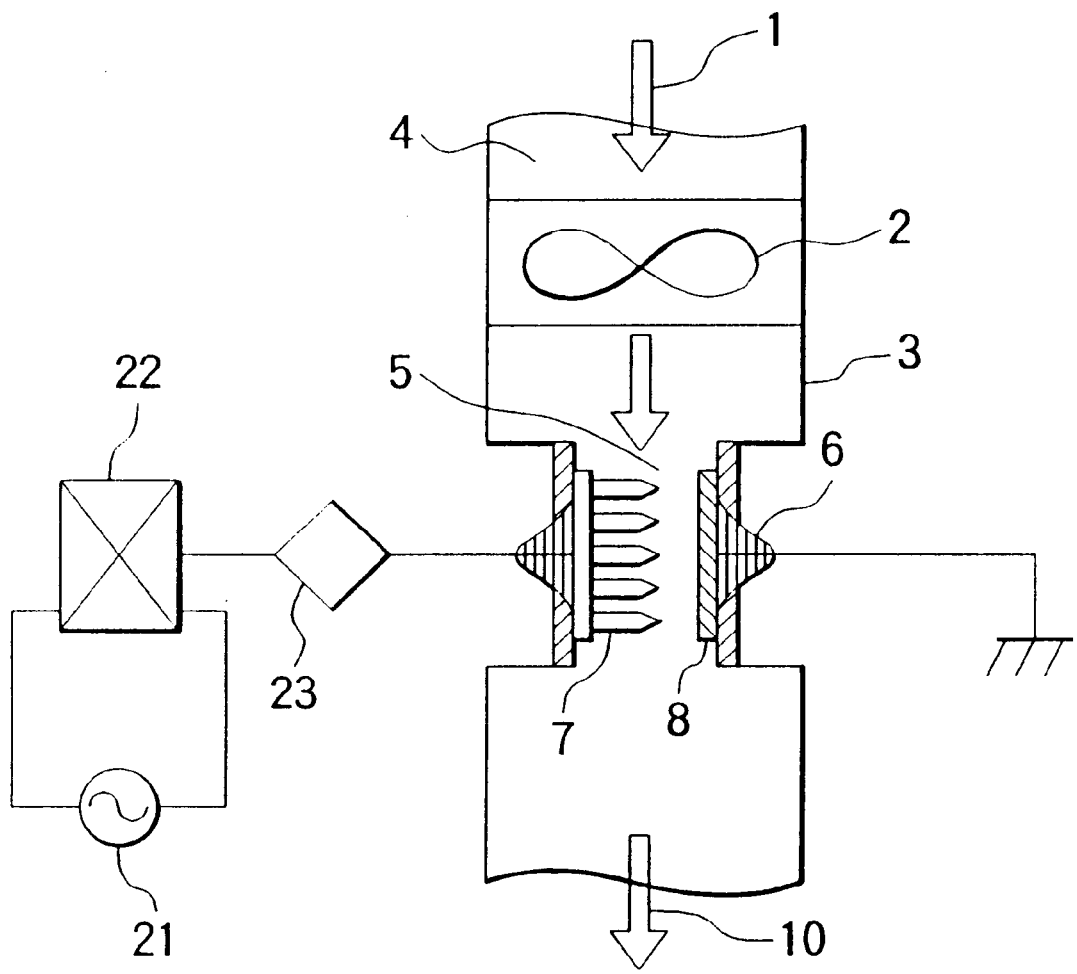
FIG. 1 is a structural drawing showing a microorganism multiplication preventing apparatus according to the embodiment 1 of the present invention.

FIG. 1 is a structural drawing showing a microorganism multiplication preventing apparatus according to the embodiment 1 of the present invention. In FIG. 1, numeral 1 denotes outdoor gas, the apparatus comprises a fan 2 provided on the downstream side of the supply port 4 for taking in the gas 1, a vent passage 3 for allowing the gas 1 taken in by the fan 2 to flow, an activated-particle generating chamber 5 provided in the vent passage 3 for ionizing and ozonizing the taken-in gas 1 with a discharge caused by application of a high voltage between the activated-particle generating electrode mentioned below, which is an ionizing chamber in this case, and a bushing 6 provided in the vent passage 3 and made of insulating materials. Numerals 7 and 8 denote activated-particle generating electrodes, wherein the former 7 denotes a metal needle electrode made of metallic material such as tungsten, stainless steel or nickel and the latter 8 denotes a ground electrode placed opposite the metal needle electrode 7 and made of metal plate. Numeral 10 denotes ozone-contained ionized gas (referred to as ionized gas). Furthermore, numeral 14 denotes an object for microorganisms to multiply thereon, the apparatus comprising an input supply source 21 for supplying the power forming the source of a high voltage for arousing a discharge near the electrode 7 by using the electrode 7, a boosting converter 22 connected to the input power source 21 for converting and boosting the primary voltage supplied from the input power source and a pulse converter 23 connected to the boosting converter 22 for pulsing the high voltage boosted by the boosting converter 22. Incidentally, in this embodiment, the input power source 21 is set at. AC 100V and a case where the AC 100V inputted is output as cathodic DC high voltage by the boosting converter 22 will be described.

Next, the operation will be described.

First, outdoor gas 1 is taken in from the supply port 4 by the fan 2 and led through the vent passage 3 into the ionization chamber 5.

In this ionization chamber 5, a plurality of metal needle electrodes 7 and a metal plate ground electrode 8 placed opposite the metal needle electrodes 7 are disposed with a space (gap length) between the both electrodes 7, 8 kept at several millimeters. Here, when a cathodic DC pulse high voltage of several kV produced by the boosting converter 22 and pulsed by the pulse converter 23 is applied to the metal needle electrodes 7, a high electric field is generated near the tip of metal needle electrodes 7 and a corona discharge takes place.

When the gas 1, containing oxygen molecules, is led into the ionization chamber 5 during this discharge, oxygen molecules contained in the gas 1 are ionized into negative ions by attaching of electrons and moreover collide with electrons to be dissociated, thereby producing ozone, so that ionized gas 10 containing both ozone and negative ions are generated.

In addition, with this embodiment, since the pulse frequency of a cathodic DC pulse high-voltage is controlled by the pulse converter 23, current flowing at the time of discharge is reduced and the production of ozone is suppressed.

Meanwhile, being highly oxidative, ozone becomes not only harmful to human bodies but also prone to corrode materials of constitutive objects with higher concentration of ozone, and therefore it is necessary to control the concentration of ozone in the ionized gas 10 below 0.1 ppm, an operating reference value at which safety is guaranteed. Furthermore, in application of such ozone-contained gas to the preservation of food, experiments revealed that a greater concentration of ozone than 0.05 ppm will deteriorate and discolor food itself and the concentration of ozone should be kept at 0.05 ppm or lower in use of ozone-contained gas.

Accordingly, with this embodiment, ionized gas 10 containing a low concentration (0.05 ppm or lower) of ozone is produced by suppressing the production of ozone in the manner mentioned above and supplied to objects 14 on which microorganisms are multiplying. In usual cases, since air is taken as supplied air 1, ionized gas 10 containing a low concentration of ozone is supplied.

On the other hand, the ion concentration in the ionized gas 10 at this time depends also on the condition of objects 14 on which microorganisms multiply, but is required to be kept on the order of hundreds of times the ion concentration (10–100 ions/cm$^3$) normally existing in air according to experiments, and the multiplication of microorganisms, (bacterial) is prevented when this concentration region is attained. However, preferably an ion concentration of not less than 1000 times, i.e., not lower than $10^4$ ions/cm$^3$, is effective to prevent the multiplication of microorganisms. Thus, ionized gas containing a higher concentration of ions than $10^4$ ions/cm$^3$ is arranged to be supplied.

Since ions and ozone are continuously supplied to the surface of an object 14 on which microorganisms multiply (are adhered) in this manner, the multiplication of microorganisms can be prevented even in a concentration range where the multiplication of microorganisms cannot be prevented by using either one alone.

Here, there will be described one experimental example implemented to prove that negative ions alone can be generated in a great amount while maintaining the ozone concentration in the ionized gas 10 to a low concentration by controlling the current flowing at the time of discharge.

Figure 2:
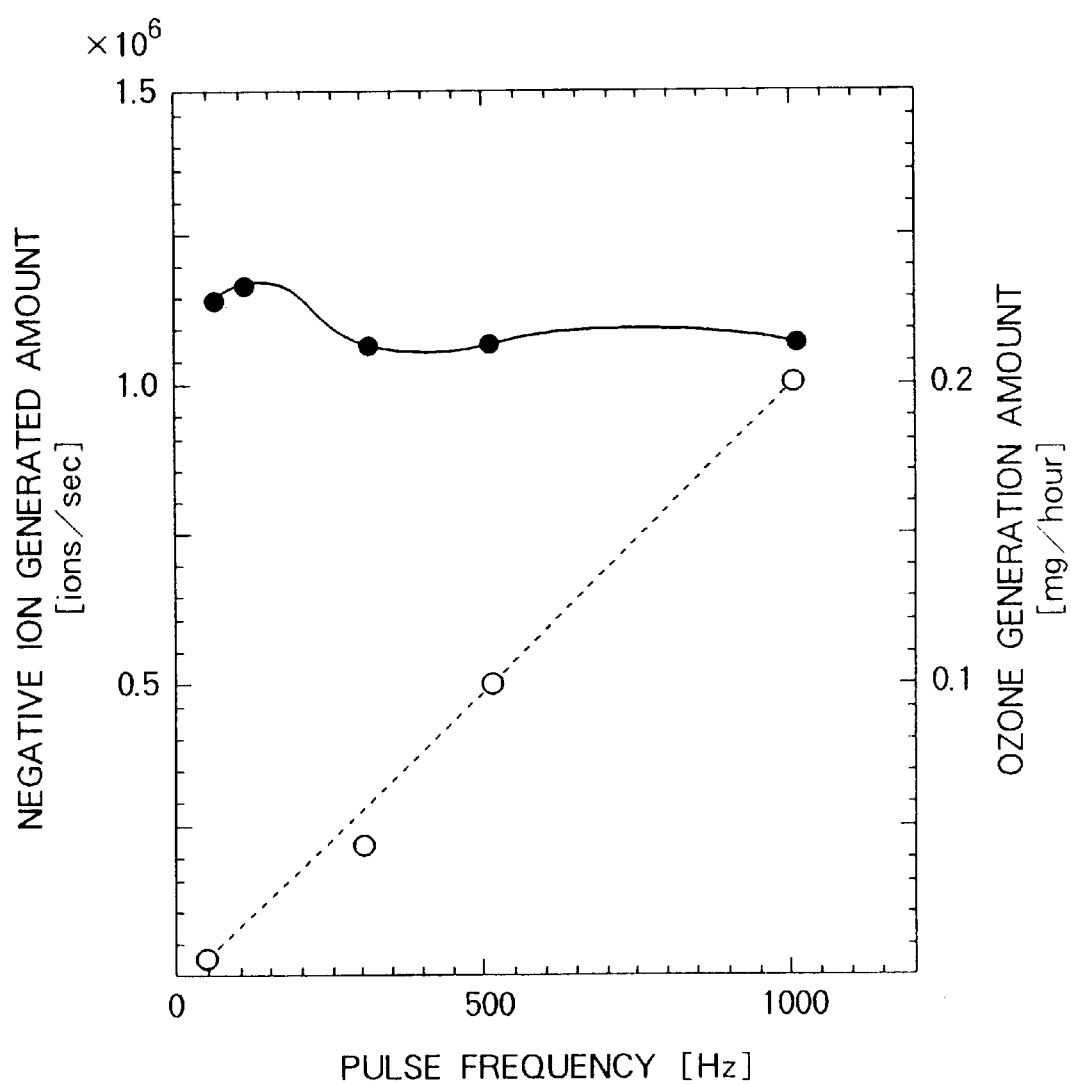
FIG. 2 is a characteristic graph showing the relation between the pulse frequencies and the produced amounts of negative ions and ozone with respect to the embodiment 1 of the present invention.

FIG. 2 is a characteristic diagram showing the relation between pulse frequencies of the applied voltage and the production of negative ions and ozone. The solid characteristic curve and broken characteristic curve represent the relation between pulse frequencies and the production of negative ions and the relation between pulse frequencies and the production of ozone, respectively. In this experimental example, measurements were carried out with five pieces of 1 cm long metal needle electrodes 7 placed at intervals of 5 mm, wherein the gap length between this metal needle electrode 7 and a 1 cm wide and 3 cm long metal plate ground electrode 8 kept at 1.0 mm, the zero peak voltage of a cathodic DC pulse high-voltage to be applied to the metal needle electrode 7 was kept at 8 kV, the wind velocity of air passing between the electrodes was kept at about 1 m/s, and the temperature and humidity of supplied air was kept at 20° C. and 60%.

As was found from FIG. 2, it was confirmed that, with rising pulse frequency, the production of ozone increases as a linear function but that of negative ions becomes almost constant.

For example, when the pulse frequency is set at 500 Hz, the concentration of negative ions in air at a gas flow rate of 50 L/min can be taken at $3\times10^6$ ions/cm$^3$ while that of ozone maintained at 0.03 ppm.

By controlling the pulse frequency in this manner, the concentration of negative ions was found to be increased while that of ozone maintained in the range of a low concentration.

Incidentally, in the experimental example mentioned above, the number of needles in the metal needle electrode 7 was set at 5 pieces for an area of 3 cm$^2$ in the metal plate ground electrode 8 but a further increase in the number of pieces can increase the production of negative ions.

In addition, with the experimental example mentioned above, the zero peak voltage of DC pulse high-voltage is set at 8 kV and the gap length is kept at 10 mm, but a further higher applied voltage or a further shorter gap length can increase the production of negative ions if they remain within a certain range (corona discharge region). At this time, however, since the production of ozone also increases simultaneously, the pulse frequency has to be lowered. Furthermore, a further higher applied voltage or a further shorter gap length beyond the range mentioned above would cause a short circuit and therefore is very dangerous.

With this experimental example, air with a wind velocity of about 1 m/s is flown between both electrodes 7 and 8, but the production of negative ions increases with higher wind velocity if the wind velocity of air is allowed to change in a range of 0.1–3.0 m/s. Since an increase in the flow rate of air flowing through the vent passage 3 leads to a decrease in the production of ozone, however, the pulse frequency has to be lowered.

Next, it will be described referring to the experimental example that the multiplication of microorganisms is suppressed by use of ionized gas 10 containing a low concentration of ozone.

TABLE 1

| Item | Mixed treatment of ions and ozone | Ion treatment | Ozone treatment | Untreated treatment |
| --- | --- | --- | --- | --- |
| Ion concentration (ions/cc) | about 10$^6$ | about 10$^6$ | — | — |
| Ozone concentration (ppm) | about 0.03 | — | about 0.05 | — |
| Number of bacteria (colon./lab.dish) | 0 | about 700 | about 800 | about 900 |

Table 1 shows the result obtained when laboratory dishes were prepared which hold bacteria (yellow staphylococcus) planted artificially on agar culture media with objects on which microorganisms multiply denoted by 14 and the treatment effect of ionized air containing negative ions and ozone was studied. Here, the concentration of negative ions in ionized gas 10, containing negative ions and ozone, supplied to a laboratory dish was set at about 10$^6$ colon./cm$^3$. At that time, the voltage applied between the electrodes in the ionized chamber 5 was kept at about 15 kV.

Meanwhile, the temperature and humidity of air 1 supplied to an object (laboratory dish) 14 on which microorganisms multiply were set at 20° C. and 80–90% and treatment was continuously made for three days by using ionized air 10 containing ca. 10$^6$ ions/cm$^3$ concentration of negative ions and 0.03 ppm of ozone.

As comparative items, a case of being treated with 20° C. air in which neither ion nor ozone is generated, a case of being treated with 20° C. ionized air at a negative ion concentration of about 10$^6$ ions/cm$^3$ and an ozone concentration of 0.02 ppm or lower and a case of being treated with 20° C. ozonized air at an ozone concentration of 0.05 ppm and a negative ion concentration of about 10$^2$ ions/cm$^3$ were added.

According to the experimental result, as shown in Table 1, the number of colonies after 3 days was about 900 colon./lab.dish in a case of being treated with 20° C. air in which neither ion nor ozone is generated and the number of colonies after 3 days was about 100 colon./lab.dish in a case of being treated with 20° C. ionized air at a negative ion concentration of about 10$^6$ ions/cm$^3$ and an ozone concentration of 0.02 ppm or lower, so that the multiplication preventing effect of microorganisms was observed. However, a stop of ion treatment allowed the number of bacteria colonies to amount to about 700 colon./lab.dish and therefore it was found that no sufficient multiplication preventing effect of microorganisms was obtained continuously by means of ion treatment. In addition, in a case of being treated with 20° C. ozonized air at an ozone concentration of 0.05 ppm and a negative ion concentration of about 10$^2$ ions/cm$^3$, the number of bacteria colonies after 3 days became about 800 colon./lab.dish and it was found that, though the multiplication of bacteria was suppressed to some extent on ozone treatment, its effect was not significant.

On the other hand, in a case of being treated with 20° C. ionized air 10 at a negative ion concentration of about 10$^6$ ions/cm$^3$ and an ozone concentration of 0.03 ppm, the number of bacteria colonies after 3 days became about 0 col./lab.dish, so that the effect of a complete multiplication prevention was obtained.

In addition, when the agar culture medium treated with ozone-contained ionized air 10 was allowed to stand at room temperatures (about 20° C.) after a stop of treatment, hardly any re-multiplication of bacteria was recognized.

As mentioned above, the above experimental result revealed that ozone-contained ionized gas 10 can increase the capability of preventing the multiplication of microorganisms by additive effect of ozone and negative ions for bacteria planted in an agar culture medium as compared with a simple use of ionized gas or ozone and moreover can exterminate bacteria.

Incidentally, Table 1 showed the effect of ionized gas containing a low concentration of ozone by using yellow staphylococcus, an aerobic micrococcus, but also for other bacteria, e.g., bacillus procyaneus having a different shape and aerobic rods, such as *E. coli* and salmonella, a similar effect was obtained.

In addition, with respect to bacillus bacteria, aerobic rods which form a spore, or must of fungi, it is considered that a similar effect is obtained and multiplication can be inhibited.

With this experimental example, the microorganism multiplication preventing effect was exhibited for treatment with ozone-contained ionized air at an ozone concentration of about 0.03 ppm and a negative ion concentration of about 10$^6$ ions/cm$^3$, but it is preferable that the concentration of negative ions and that of ozone in ozone-contained ionized gas 10 to be supplied are changed depending on the type of microorganisms existing on the surface of an object 14 and the treatment method.

Incidentally, with the embodiment mentioned above, the effect was shown for a treatment with ozone- and negative-ion-contained ionized air, but a similar effect is obtained also in a case where a high anodic DC pulse voltage is generated by means of the boosting converter 22 and the pulse converter 23, the high anodic DC pulse voltage is applied to the metal needle electrode 7 in the ionization chamber 5 to produce positive ions and ozone, and the ionized gas 10 containing these ozone and positive ions is arranged to be supplied to objects 14 on which microorganisms multiply. However, negative ions have a greater effect of preventing the multiplication of microorganisms than anodic ions.

In addition, a similar effect is obtained also in a case where a high AC pulse voltage is generated by means of the boosting converter 22 and the pulse converter 23, the high anodic AC pulse voltage is applied to the metal needle electrode 7 in the ionization chamber 5 to produce negative ions, positive ions and ozone, and the ionized gas 10 containing these ozone and positive and negative ions is arranged to be supplied to objects 14 on which microorganisms multiply. However, when negative ions and positive ions are contained in equal amounts in the ionized gas 10, positive ions and negative ions recombinate and annihilation of ions is accelerated, so that the effect of preventing the multiplication of microorganisms decreases. Thus, it is desired to allow only monopolar ions to be produced.

In addition, with the embodiment mentioned above, arrangements in which treatment proceeds while the ion concentration and ozone concentration were maintained constant during a period of treatment was shown, but objects 14 on which microorganisms multiply may be treated while the ion concentration is kept to a high concentration and the ozone concentration alone allowed to change by changing the value of the pulse frequency during a period of treatment.

Figure 3A:
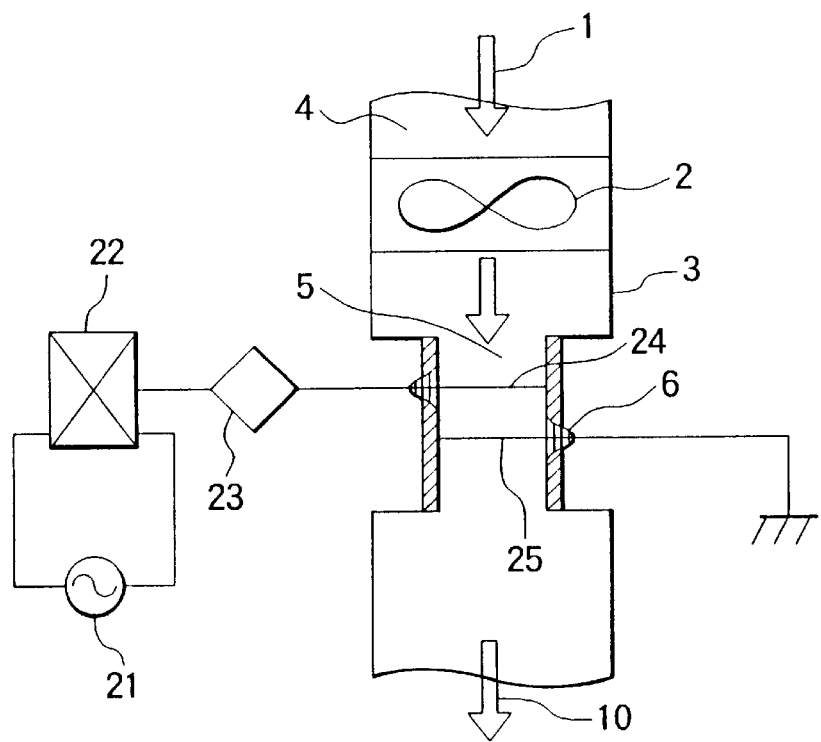
FIGS. 3a, 3b are structural drawings showing a modified example of the microorganism multiplication preventing apparatus according to the embodiment 1 of the present invention.
Figure 3B:
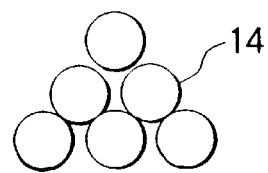

Furthermore, the above experimental example showed a case where a metal needle electrode 7 and a metal plate ground electrode 8 placed opposite the metal needle electrode 7 were provided, but a similar effect was observed also for a discharge occurring when a plurality of metal fine wires 24 (See FIG. 3a) of about 0.1–0.2 mm diameter and a metal-grade-shaped ground electrode 25 placed opposite these metal fine wires 24 were provided, and a high cathodic DC pulse voltage was applied to these metal fine wires 24. FIG. 3(a) is a structural drawing showing a modified example of microorganism multiplication preventing apparatus according to the embodiment 1 of the present invention and FIG. 3(b) is a sectional schematic showing the portion of metal fine wires 24.

Embodiment 2

Figure 4:
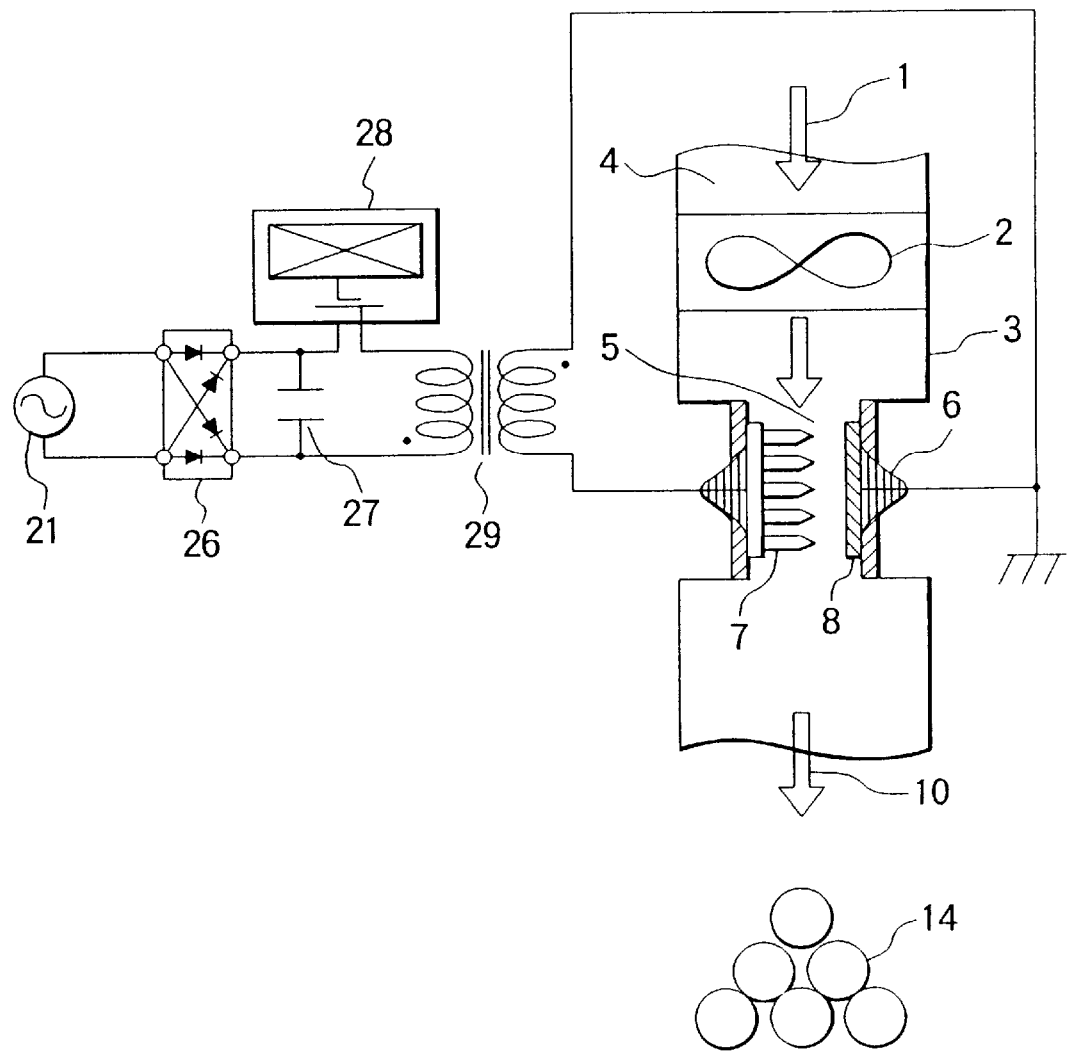
FIG. 4 is a structural drawing showing a microorganism multiplication preventing apparatus according to the embodiment 2 of the present invention.

FIG. 4 is a structural drawing showing a microorganism multiplication preventing apparatus according to the embodiment 2 of the present invention. In FIG. 4, the apparatus comprises a rectifier 26 for converting the AC voltage supplied from the input power source 21 into a DC voltage, a capacitor 27 for accumulating the DC voltage, a pulse oscillator 28 for pulsing the DC voltage and a pulse transformer 29 for boosting the DC pulse voltage, wherein a pulse generator comprises the capacitor 27, the pulse oscillator 28 and pulse transformer 29. Incidentally, when the voltage supplied from the input power source 21 is DC voltage, there is no need for a rectifier 26.

Next, the operation will be described.

First, outdoor gas 1 is taken in from the supply port 4 by the fan 2 and led through the vent passage 3 into the ionization chamber 5.

In this ionization chamber 5, a plurality of metal needle electrodes 7 and a metal plate ground electrode 8 attached in close adhesion to the dielectric 9 placed opposite the metal needle electrodes 7 are disposed with the space (gap length) between the both electrodes 7, 8 kept at several mm.

An AC voltage is supplied from the input power source 21 to the rectifier 26, where it is converted into DC voltage. The DC voltage is stored in the capacitor 27 and the pulse oscillator 28 pulses it into DC pulse voltage, which is supplied to the pulse transformer 29. When DC pulse high voltage from the pulse transformer 29 is applied to the metal needle electrodes 7, a high electric field is generated near the tip of metal needle electrodes 7 and a corona discharge takes place.

And, when the gas 1, containing oxygen molecules, is led into the ionization chamber 5 during this discharge, oxygen molecules contained in the gas 1 are ionized into negative ions by attaching of electrons and moreover collide with electrons to be dissociated, thereby producing ozone, so that ionized gas containing both ozone and negative ions are generated.

And since the pulse frequency of a high cathodic DC pulse voltage applied to the metal needle electrode 7 is controlled by the pulse generator 28, current flowing at the time of discharge is reduced and the production of ozone is suppressed.

Meanwhile, since ozone is highly oxidative and becomes harmful with higher concentration of ozone as mentioned above, the concentration of ozone in the ionized gas 10 is controlled to 0.1 ppm or lower.

In this manner, ionized gas 10 containing a low concentration of ozone is produced and supplied to objects 14 on which microorganisms are multiplying. In normal cases, since air is employed as the supplied gas, ionized gas 10 containing a low concentration of ozone is supplied.

As a result, since ions and ozone are continuously supplied to the surface of an object 14 on which microorganisms have multiplied, the multiplication of microorganisms can be prevented even in a concentration range where the multiplication of microorganisms cannot be prevented by using either one alone.

Incidentally, with this embodiment, after pulsed by means of the pulse oscillator 28, DC voltage is boosted by means of the pulse transformer 29 to generate a high DC pulse voltage, so that high-voltage resistivity becomes unnecessary in use of a pulse oscillator 28 and the cost of the apparatus is reduced.

Embodiment 3

Figure 5:
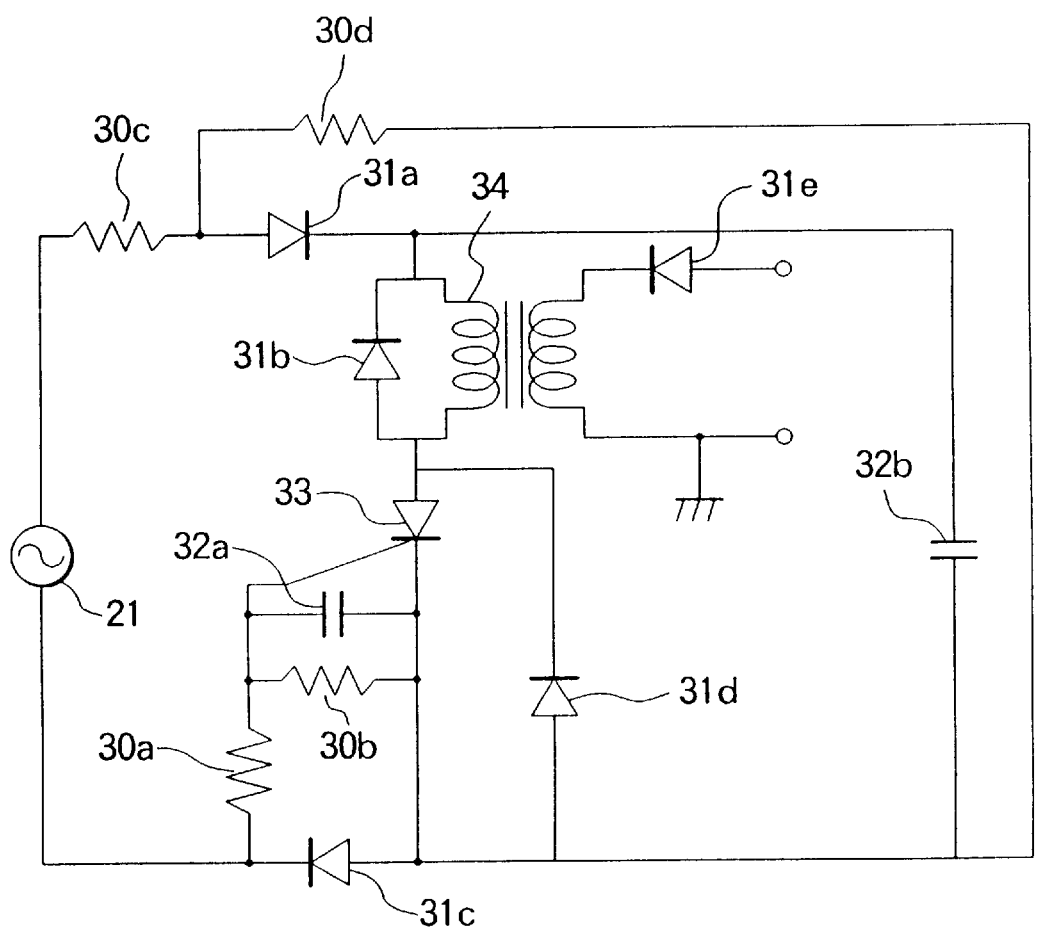
FIG. 5 is a circuit diagram showing the configuration of a pulse generator of a microorganism multiplication preventing apparatus according to the embodiment 3 of the present invention.

In the embodiment 2 mentioned above, an arrangement in which, after being pulsed by means of the pulse oscillator 28, DC voltage is boosted by means of the pulse transformer 29 to generate a high DC pulse voltage was shown, but a similar effect can be obtained even if a high DC pulse voltage is arranged to be produced by using an electric circuit as shown in the circuit diagram of FIG. 5. As shown in FIG. 5, the pulse generator comprises resistors 30a–30d, diodes 31a–31e, capacitors 32a and 32b, a thyristor 33 and a boosting transformer 34.

Next, the operation will be described. The AC voltage supplied from the input power source 21 is converted into half-wave voltage by the diode 31a and charged in the capacitor 32b. When the capacitor 32b is charged with electricity, a signal is sent to the thyristor 33 by a switch section comprising the capacitor 32a and the resistor 30b and current begins to flow through the thyristor 33, then the electric charge accumulated in the capacitor 32b flows through the primary coil of the boosting transformer 34. When current flows through the primary coil, an electromotive force takes place and a high AC pulse voltage is generated. The generated high AC pulse voltage is half-wave rectified by the diode 31e and converted into a high DC pulse voltage.

With this embodiment, no use of a pulse transformer is needed and a normal transformer can be employed, so that the apparatus is handy and its cost can be reduced.

Embodiment 4

Figure 6:
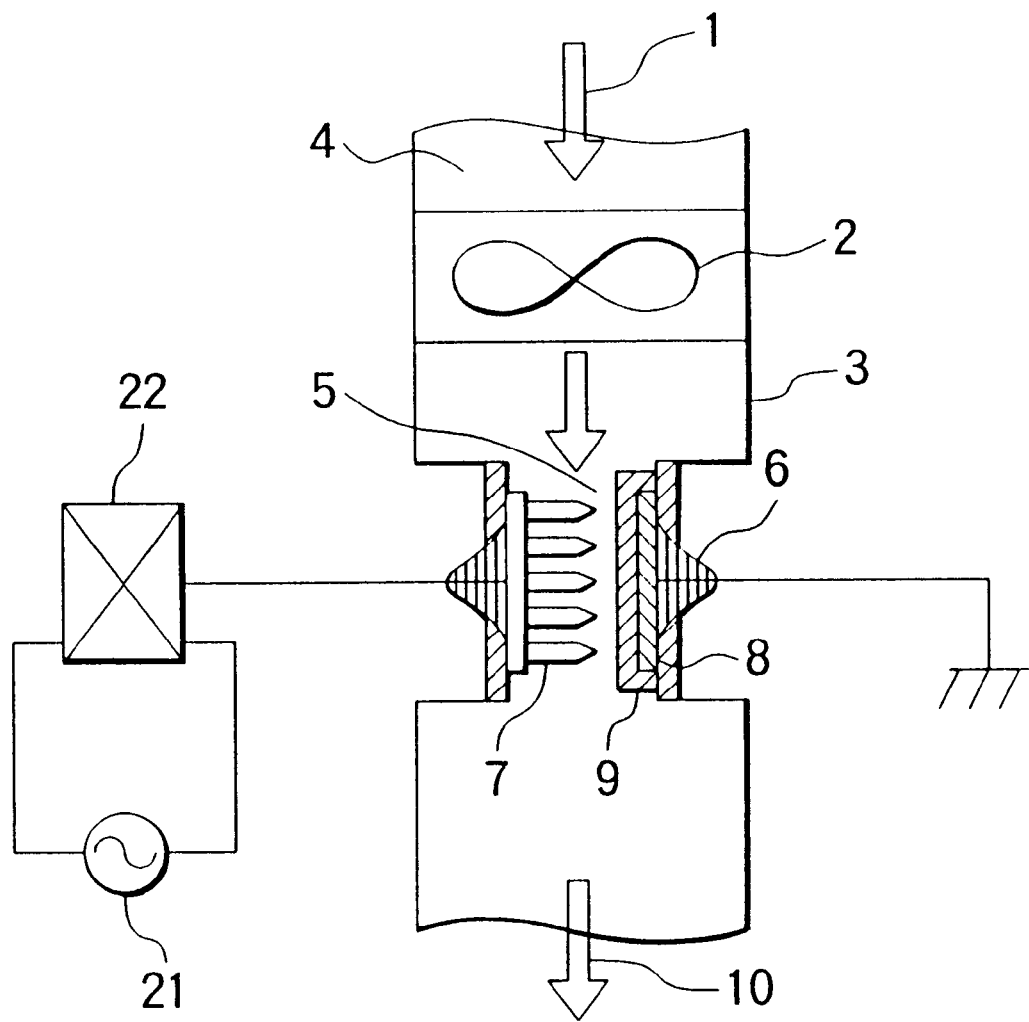
FIG. 6 is a structural drawing showing a microorganism multiplication preventing apparatus according to the embodiment 4 of the present invention.

With the first embodiment mentioned above, there was an example of cases where a high cathodic DC pulse voltage is arranged to be applied to the metal needle electrode 7 in the ionization chamber 5 and ionized gas 10 with the concentration of ozone kept low and that of negative ions elevated as much as possible, was generated by controlling the current flowing at the time of discharge, but also with an arrangement in which a plate-shaped dielectric 9 made of dielectric material, such as ceramic, glass or quartz is attached on the metal plate ground electrode 8 placed opposite the metal needle electrode 7 by vapor deposition or close adhesion, and current flowing at the time of discharge is suppressed under application of a high DC voltage as shown in the structural drawing of FIG. 6. Ionized gas 10, with the concentration of ozone kept low and that of negative ions elevated as much as possible, can be generated and a similar microorganism multiplication preventing apparatus can be obtained. The dielectric 9 acts as discharge current control means.

Here, there will be another experimental example that was executed to prove that the amount of ozone produced at a microorganism multiplication preventing apparatus according to this embodiment 4 can be reduced by use of a dielectric 9 evaporatively deposited on the metal plate ground electrode 8.

With this experimental example, 5 pieces of 1 cm metal needle electrodes 7 are placed at intervals of 5 mm, the gap length between the metal needle electrodes 7 and a 1 cm wide and 3 cm long metal plate ground electrode 8 with a 0.5 cm thick dielectric 9 closely adhered thereon are kept at 10 mm, the zero peak voltage of high cathodic DC voltage applied to the metal needle electrode 7, the wind velocity of air passing between the both electrodes, and the temperature and humidity of supplied air are set at 8 kV, about 50 cm/s, and 20° C. and 60%, respectively.

Under these conditions, ions were generated and the amount of ions produced were measured. According to the result of the measurements, the amount of ions produced was about $1\times10^9$ ions/s and became about $3\times10^9$ ions/s on removal of the dielectric 9, which confirmed that the produced amount of ions was nearly equal regardless of the presence of a dielectric 9.

On the other hand, the produced amount of ozone to be generated simultaneously by a discharge was about 1 mg/hr without provision of a dielectric, but the produced amount of ozone was reduced to about 0.01 mg/hr by the provision of a dielectric.

As is clear from the above, according to this embodiment 4, the concentration of ozone can be suppressed at a low value while that of negative ions in ionized gas 10 is maintained to be sufficiently high.

In addition, with this embodiment 4, because the amount of ozone produced is reduced and controlled by only a change in the thickness of a dielectric 9 without use of a pulse converter 23, there is an advantage that the apparatus arrangement is simple and the apparatus can be easily and inexpensively fabricated.

Embodiment 5

Figure 7:
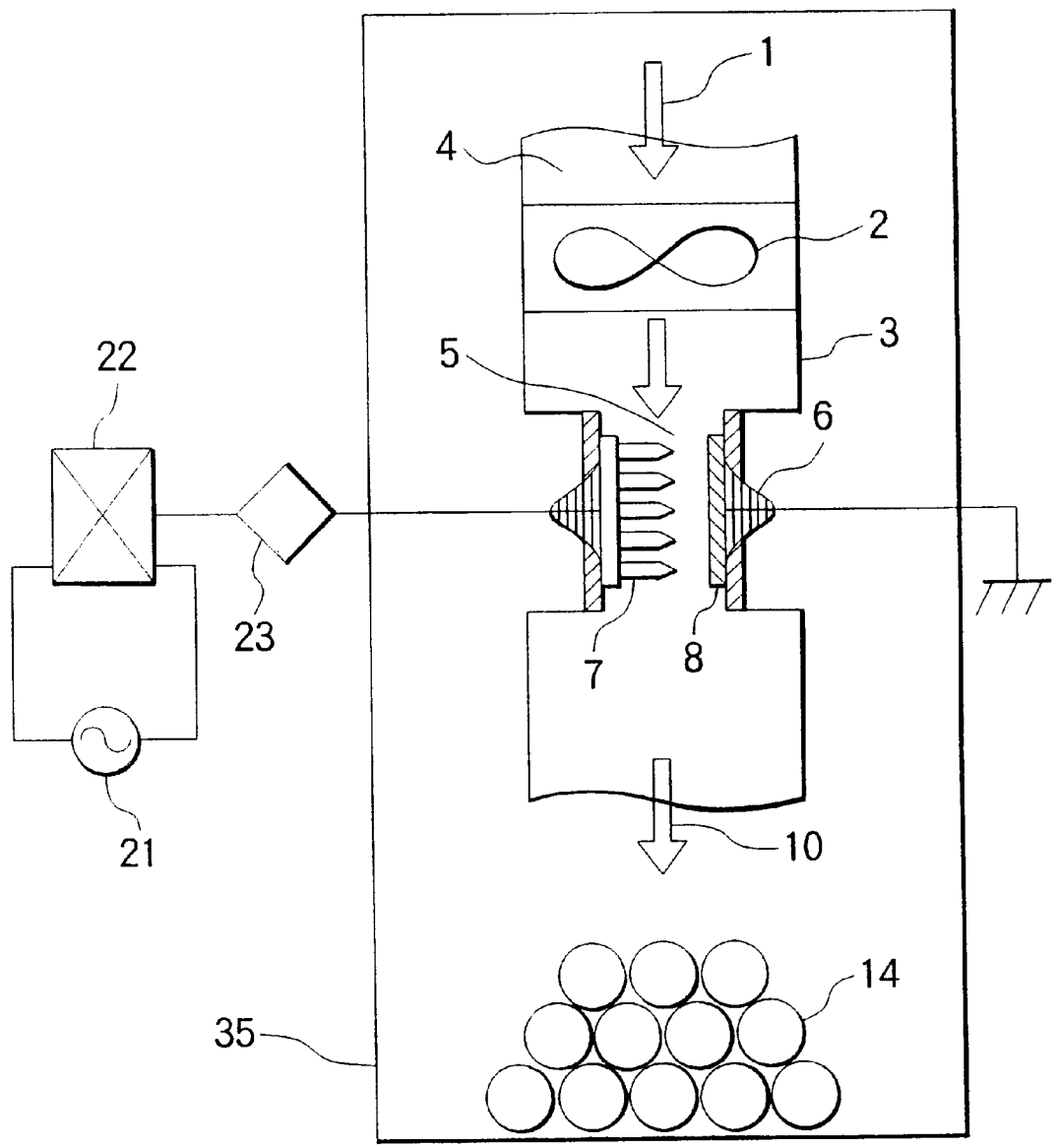
FIG. 7 is a structural drawing showing a microorganism multiplication preventing apparatus according to the embodiment 5 of the present invention.

FIG. 7 is a structural drawing showing a microorganism multiplication preventing apparatus according to the embodiment 5 of the present invention. In FIG. 7, Numeral 35 denotes an ion supply chamber having a space for housing objects 14 for microorganisms to multiply thereon to which the ionized gas 10 containing the ozone generated in the ionization chamber 5 is supplied.

Next, the operation will be described.

First, outdoor gas 1 is taken in from the supply port 4 by the fan 2 and led through the vent passage 3 into the ionization chamber 5.

In this ionization chamber 5, a plurality of metal needle electrodes 7 and a metal plate ground electrode 8 placed opposite the metal needle electrodes 7 are disposed with a space (gap length) between both electrodes 7, 8 kept at several millimeters. Here, when a high cathodic DC pulse voltage of several kV produced by the boosting converter 22 and pulsed by the pulse converter 23 is applied to the metal needle electrodes 7, a high electric field is generated near the tip of metal needle electrodes 7 and a corona discharge takes place.

Thus, when the gas 1, containing oxygen molecules, is led into the ionization chamber 5 during this discharge, oxygen molecules contained in the gas 1 are ionized into negative ions by the attaching of electrons and moreover, collide with electrons, to be dissociated, thereby producing ozone, so that ionized gas 10 containing both ozone and negative ions are generated.

And at this time, since the pulse frequency of a high cathodic DC pulse voltage applied to the metal needle electrode 7 is controlled by the pulse converter 23, current flowing at the time of discharge is reduced and the production of ozone is suppressed.

Meanwhile, since ozone is highly oxidative and becomes harmful with higher concentration of ozone, the concentration of ozone in the ionized gas 10 is controlled to 0.1 ppm or lower.

In this manner, ionized gas 10 containing a low concentration of ozone is produced and released to the ion supply chamber 35. In normal cases, since air is employed as the supplied gas, ionized gas 10 containing a low concentration of ozone is supplied.

Since ions and ozone are continuously supplied to the surface of objects 14 on which microorganisms have multiplied and into the space for housing the objects 14 as above, the additive effect of ions and ozone enables the microorganisms already existing on the surface of objects 14 and those which float in the space inside the ion supply chamber 35, to fall on the surface of objects 14 and begin to newly multiply to be prevented from multiplication.

Next, the following describes the experimental example where the multiplication of microorganisms is inhibited by the use of ionized gas 10 containing a low concentration of ozone.

TABLE 2

| Item | Mixed treatment of ions and ozone | Ion treatment | Ozone treatment | Untreated treatment |
|---|---|---|---|---|
| Ion concentration (ions/cc) | about $10^5$ | about $10^5$ | — | — |
| Ozone concentration (ppm) | about 0.05 | — | about 0.2 | — |
| Number of bacteria (colon./cm²) | about 300 | about 1000 | about 600 | about 1600 |

Table 2 shows the experimental result of this experimental example. In the experiment, sliced raw tuna was employed as object 14 for microorganisms to multiply thereon, preserved in an ion supply chamber 35, in this case, under conditions of 0° C. and 85–95% humidity for 3 days in a refrigerator and continuously treated with the air containing ozone and negative ions produced in the ionization chamber 5.

Meanwhile, a voltage of about −10 kV was applied to the metal needle 7 in the ionization chamber 5 and the concentration of negative ions and ozone in the ion supply chamber 35 were kept at about $10^5$ ions/cm$^3$ and about 0.05 ppm.

As comparative items, a case of being treated with 0° C. air in which neither ion nor ozone is generated, a case of being treated with 20° C. ionized air at a negative ion concentration of about $10^5$ ions/cm$^3$ and an ozone concentration of 0.02 ppm or lower and a case of being treated with 0° C. ozonized air at an ozone concentration of about 0.2 ppm and a negative ion concentration of about $10^2$ ions/cm$^3$ were added. Incidentally, sampling of general bacteria from the surface of the sliced raw tuna 14 was made by the stamp method and standard agar culture media were employed as culture media.

According to the experimental result, as shown in Table 2, the number of colonies after 3 days was about 1600 colon./cm$^2$ in a case of being treated with air in which neither ion nor ozone is generated and the number of colonies after 3 days was about 1000 colon./cm$^2$ in a case of being treated with ionized air at a negative ion concentration of about $10^5$ ions/cm$^3$ and an ozone concentration of 0.002 ppm or lower, so that the bacteria inhibiting effect was somewhat observed but the effect proved to be not so much.

In addition, in a case of being treated with ozonized air at an ozone concentration of 0.2 ppm and a negative ion concentration of about $10^2$ ions/cm$^3$, the number of bacteria colonies after 3 days became about 600 colon./cm$^2$ and the multiplication of bacteria was inhibited to a considerable extent. Therefore, the experiments revealed that the concentration of ozone equal to or less than 0.2 ppm will be useful to prevent bacteria from breedeng. In treatment with ozone, however, there occurred a problem that the appearance of sliced raw tuna discolored into dark red and the quality deteriorates significantly due to the strong oxidation action of ozone.

On the other hand, in a case of being treated with 0° C. ozonized air at a negative ion concentration of about $10^5$ ions/cm$^3$ and an ozone concentration of 0.05 ppm, the number of bacteria colonies after 3 days became about 300 colon./cm$^2$ in a lab.dish and the multiplication of bacteria was inhibited to a considerable extent. Furthermore, even 3 days later from treatment, no change in appearance was observed, no putrefactive odor was sensed, and the initial freshness was recognized to be nearly perfectly maintainable.

According to the result of the experiments mentioned above, it is clear that ionized air containing a low concentration of ozone and a high concentration of negative ions permits the microorganisms existing on the surface of sliced raw tuna to be prevented from multiplication without the discoloration/denaturation of sliced raw tuna, unlike treatment with a high concentration of ozone, and the initial freshness to be retained.

With the embodiment 5, an arrangement was shown in which treatment is carried out with the ion and ozone concentrations kept constant during treatment, but even another arrangement provides much the same effect, though somewhat reducing the microorganism multiplication preventive effect, in which a continuous ion treatment and an intermittent ozone treatment is carried out with only the ozone concentration allowed to change while the ion concentration is kept constant.

Embodiment 6

Figure 8:
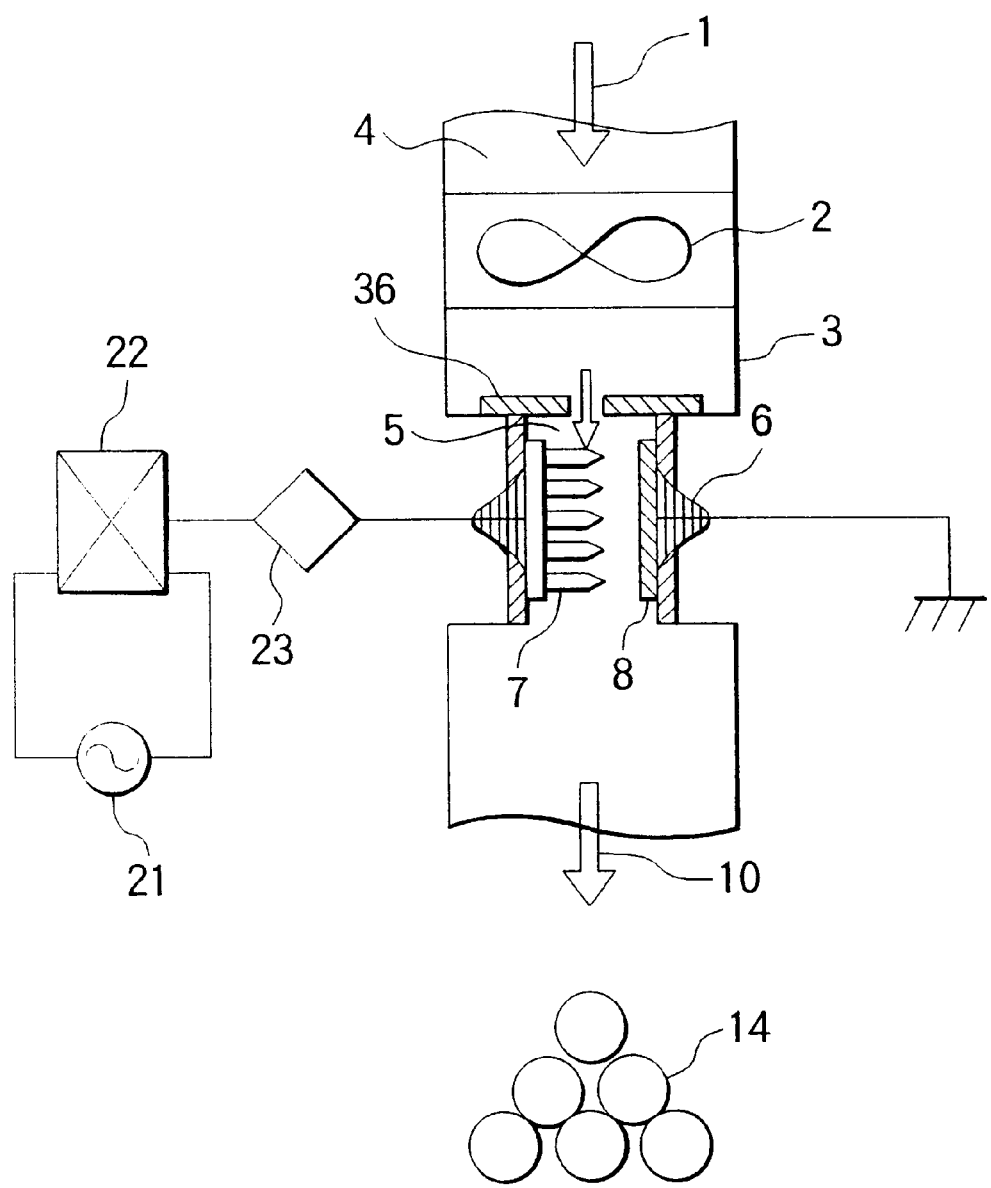
FIG. 8 is a structural drawing showing a microorganism multiplication preventing apparatus according to the embodiment 6 of the present invention.

FIG. 8 is a structural drawing showing a microorganism multiplication preventing apparatus according to the embodiment 6 of the present invention. In FIG. 8, Numeral 36 denotes gas flow control means, which is a gas flow direction control board for allowing a forcible flow of gas 1 in the space between the metal needle electrode 7 and the metal plate ground electrode 8 and accelerating the flow velocity of gas 1 flowing between both electrodes 7 and 8 at the same time by narrowing the section of a gas flow passage.

Next, the operation will be described.

First, outdoor gas 1 is taken in from the supply port 4 by the fan 2 and led through the vent passage 3 to the gas flow direction control board 36.

The gas 1, led to this gas flow direction control board 36, is changed in flowing direction by the gas flow direction control board 36 and supplied to a discharge space between a plurality of metal needle electrodes 7 provided in the ionization chamber 5 and a metal plate ground electrode 8 placed opposite the metal needle electrodes 7. Here, when a high cathodic DC pulse voltage of several kV produced by the boosting converter 22 and pulsed by the pulse converter 23 is applied to the metal needle electrodes 7, a high electric field is generated near the tip of metal needle electrodes 7 and a corona discharge takes place.

Then, when the gas 1, containing oxygen molecules, is led into the ionization chamber 5 during this discharge, oxygen molecules contained in the gas 1 are ionized into negative ions by attaching of electrons and moreover collide with electrons to be dissociated, thereby producing ozone, so that ionized gas 10 containing both ozone and negative ions are generated.

At this time, the relation of the gas flow velocity of gas 1 flowing between the metal needle electrodes and the metal plate ground electrode to the produced amounts of ozone and negative ions was studied experimentally. The obtained result revealed that, with an increase in the flow velocity of gas, the produced amount of negative ions increases, but the produced amount of ozone is invariant.

From these it become clear that elevating the flow velocity of gas 1 flowing between the metal needle electrodes 7 and the metal plate ground electrode 8 permits a high concentration of negative ions to be generated in gas 1 while the produced amount of ozone is suppressed.

With this embodiment 6, since current flowing during discharge is arranged to be suppressed and the flow velocity of gas flowing between the metal needle electrodes 7 and the metal plate ground electrode 8 is raised by using the gas flow direction control board 36, the amount of negative ions produced can be increased better while the ozone concentration is kept at a low value by suppressing the generation of ozone, and ionized gas containing a higher concentration of negative ions is obtained.

When the ionized gas 10 containing a low concentration of ozone and a high concentration of negative ions, produced in this manner, is supplied to objects 14 on which microorganisms are multiplying, the multiplication of microorganisms is inhibited by an additive effect of ions and ozone as with the embodiments mentioned above.

Incidentally, in view of preventing the annihilation of produced ions due to collision, it is desirable that the gas flow direction control board 36 is provided at a point upstream of the ionization chamber 5.

Embodiment 7

Figure 9:
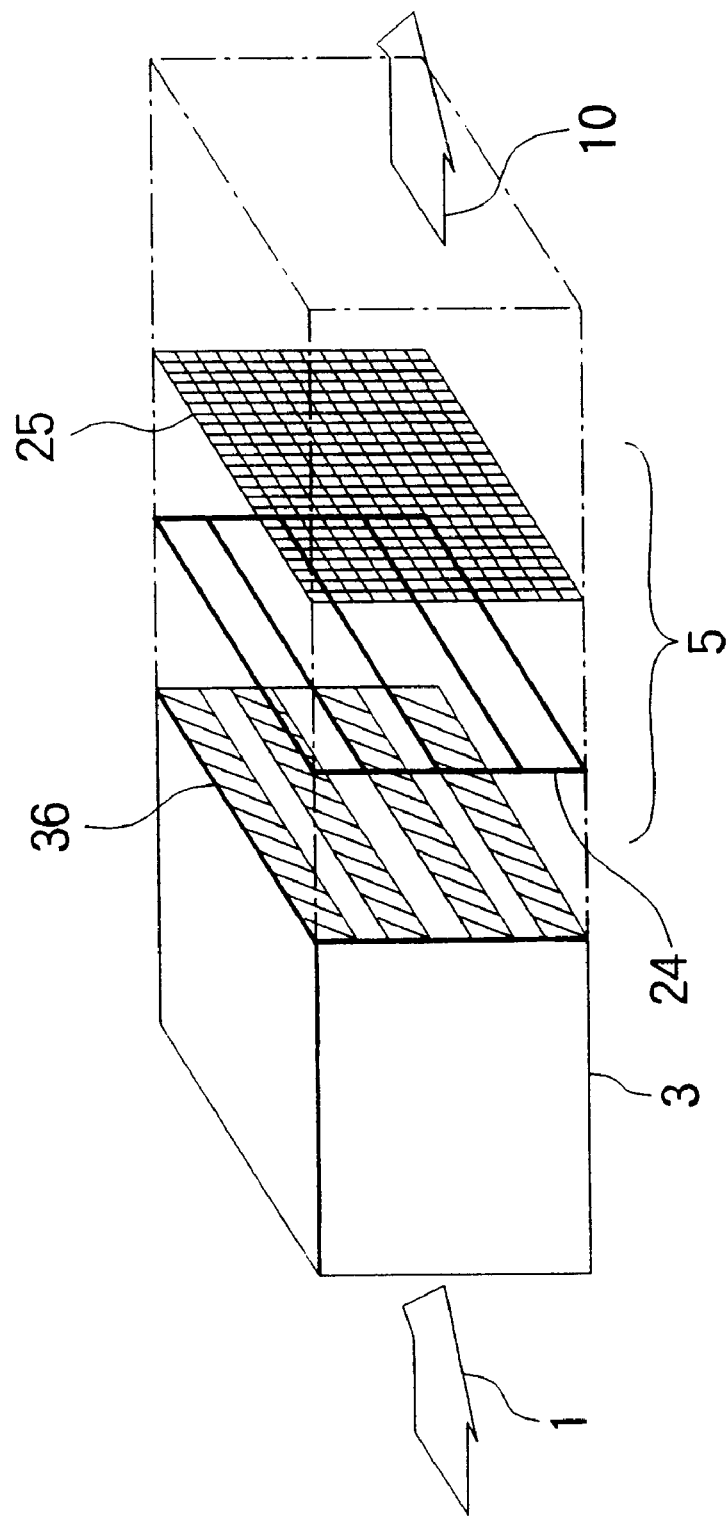
FIG. 9 is a schematic perspective showing the configuration of the ionization chamber portion of a microorganism multiplication preventing apparatus according to the embodiment 7 of the present invention.

With the embodiment 6, there was shown an arrangement in which gas 1 is let to flow in a discharge space between the metal needle electrodes 7 and the metal plate ground electrode 8 by using a gas flow direction control board 36, but a similar effect is obtained also with an arrangement in which, with a plurality of fine metal wires 24 (See FIG. 9), about 0.1–0.2 mm in diameter, and a metal grating ground electrode 25 placed opposite the these fine metal wires 24 being provided, gas 1 is allowed to flow only near the fine metal wire electrode 24 by the provision of a gas flow direction control board 36 on the upstream side of these fine metal wires 24 and the flow velocity of gas 1 is made faster by narrowing the gas flow passage.

In addition, by employing fine metal wires for a discharge electrode, there is an advantage that a pressure loss in flowing near the fine metal wires of gas 1, can be reduced and a great amount of gas can be let to flow.

Embodiment 8

Figure 10:
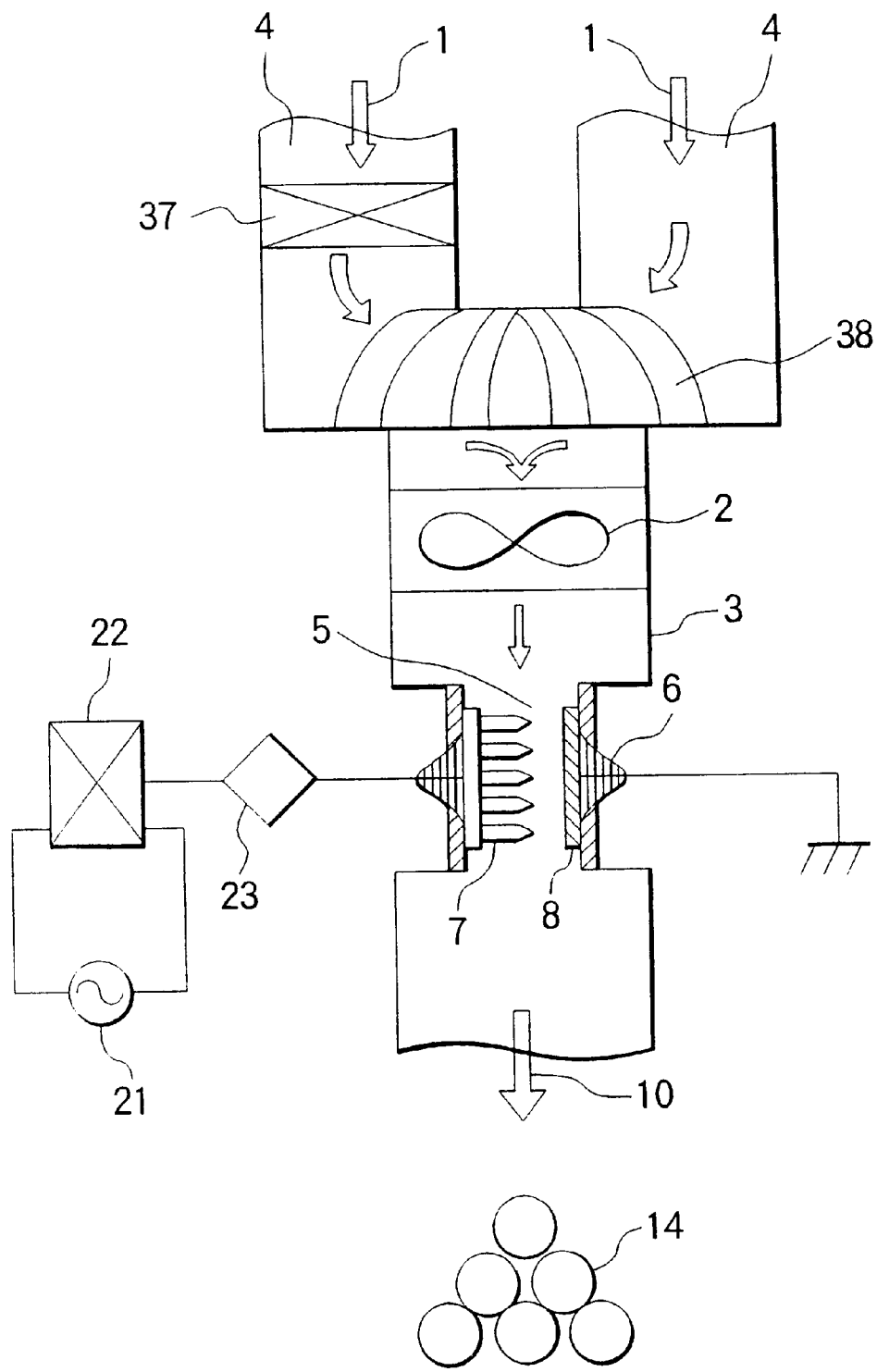
FIG. 10 is a structural drawing showing a microorganism multiplication preventing apparatus according to the embodiment 8 of the present invention.

FIG. 10 is a structural drawing showing a microorganism multiplication preventing apparatus. In FIG. 10, Numeral 37 denotes an ozone decomposition device provided in one side of the vent passage for decomposing ozone in the gas 1 taken in by using the fan 2, for which an ozone decomposition catalyzer such as manganese dioxide and activated alumina is used in this embodiment. Numeral 38 denotes a gas flow rate control device provided at the meeting portion of one vent passage and another vent passage for controlling the ratio of the flow rate of the gas 1 not passing through the ozone decomposition device 37, to regulate the ozone concentration in the gas taken into the ionization chamber 5. These ozone decomposition device and gas flow rate control device constitute ozone concentration regulating means.

Next, the operation will be described.

First, using the fan 2 and the gas flow rate control device 38, the gas 1 flowing and that not flowing through the ozone decomposition device 37 are mixed at a certain mixing ratio and taken in, then being led through the vent passage 3 into the ionization chamber 5.

In this ionization chamber 5, a plurality of metal needle electrodes 7 and a metal plate ground electrode 8 placed opposite the metal needle electrodes 7 are disposed with a space (gap length) between both electrodes 7, 8 kept at several millimeters. Here, when a high cathodic DC pulse voltage of several kV produced by the boosting converter 22 and pulsed by the pulse converter 23 is applied to the metal needle electrodes 7, a high electric field is generated near the tip of metal needle electrodes 7 and a corona discharge takes place.

Thus, when the gas 1, containing oxygen molecules, is led into the ionization chamber 5 during this discharge, oxygen molecules contained in the gas 1 are ionized into negative ions by attaching of electrons, and moreover collide with electrons to be dissociated, thereby producing ozone, so that ionized gas 10 containing both ozone and negative ions are taken out.

At this time, since the concentration of ozone in the gas 1 sucked into the ionization chamber 5 is arranged to be kept constant by using the ozone decomposition device 37 and the gas flow rate control device 38, ionized gas 10 containing a constant concentration of ozone can be supplied to objects 14 on which microorganisms are multiplying only by letting ozone be generated in a constant amount in the ionization chamber 5.

In this way, the concentration of ozone in ionized gas 10 containing the ozone supplied to objects 14 on which microorganisms multiply, becomes easy to control and moreover the concentration of ozone can be kept low, whose high value becomes harmful, so that the multiplication of microorganisms can be prevented safely and efficiently.

Embodiment 9

Figure 11:
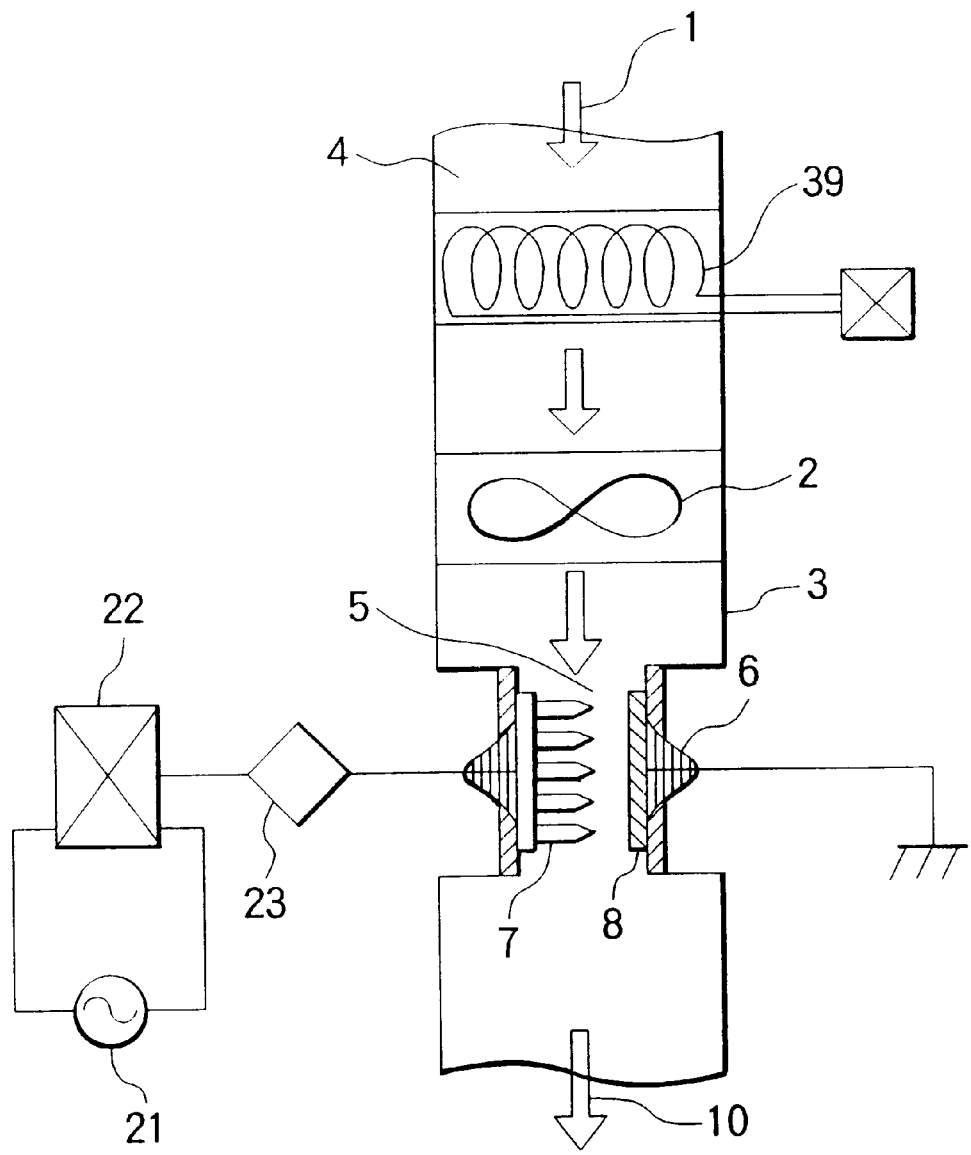
FIG. 11 is a structural drawing showing a microorganism multiplication preventing apparatus according to the embodiment 9 of the present invention.

With the embodiment 8, there was shown an arrangement in which the concentration of ozone in the gas 1 sucked into the ionization chamber 5 is kept constant by using the ozone decomposition device 37 and the gas flow rate control device 38, but a similar effect is obtained also with an arrangement in which, with a heating electric wire 39 for the decomposition of ozone provided on the upstream side of the ionization chamber 5, a fixed amount of ozone in the gas 1 is always decomposed by controlling the temperature of the heating electric wire for the decomposition of ozone to be constant to keep the concentration of ozone in the gas 1 sucked into the ionization chamber as shown in the structural drawing of FIG. 11.

In addition, the number of parts can be reduced and the constitution of an apparatus is simplified, thus facilitating control.

Embodiment 10

Figure 12:
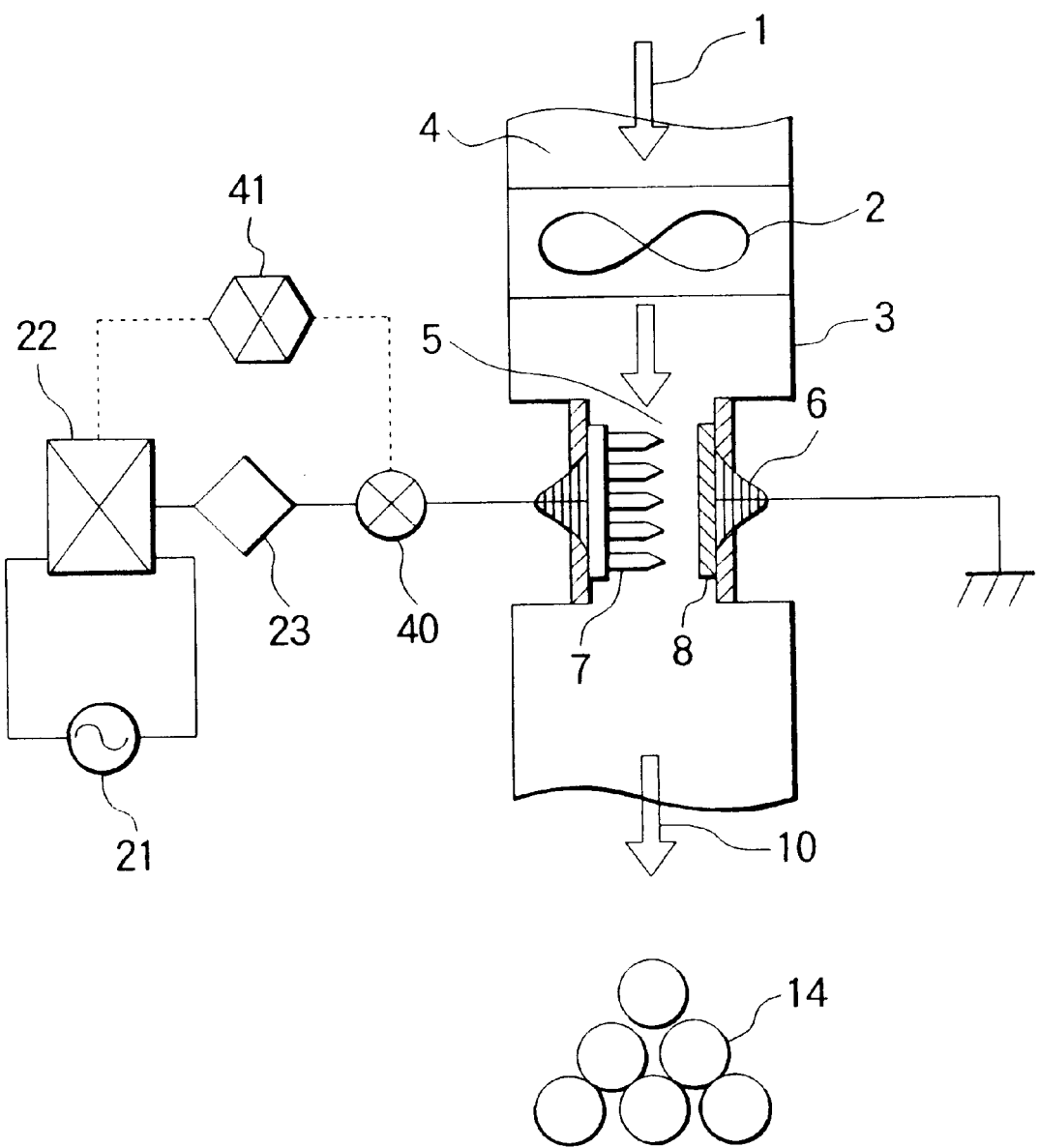
FIG. 12 is a structural drawing showing a microorganism multiplication preventing apparatus according to the embodiment 10 of the present invention.

FIG. 12 shows the structure of a microorganism multiplication preventing apparatus according to the embodiment 10 of the present invention. Numeral 40 denotes an ammeter for measuring the current flowing into the metal needle electrodes 7, and 41 denotes a control device for sending output signals to the boosting converter 22 in response to input signals from the ammeter 40.

Next, the operation will be described.

First, outdoor gas 1 is taken in from the supply port 4 by the fan 2 and led through the vent passage 3 to the ionization chamber 5.

In this ionization chamber 5, a plurality of metal needle electrodes 7 and a metal plate ground electrode 8 placed opposite the metal needle electrodes 7 are disposed with a space (gap length) between both electrodes 7, 8 kept at several millimeters. Here, when a high cathodic DC pulse voltage of several kV produced by the boosting converter 22 and pulsed by the pulse converter 23 is applied to the metal needle electrodes 7, a high electric field is generated near the tip of the metal needle electrodes 7 and a corona discharge takes place, so that ionized gas 10 containing a low concentration of ozone and a high concentration of negative ions are produced.

Incidentally, with this embodiment, a value of current flowing to the metal needle electrodes 7 is measured at this time by using the ammeter 40. And, when a value of current is recognized to tend toward an increase, a signal is sent from the ammeter 40 to the control device 41 and in turn from the control device 41 to the boosting converter 22 to reduce the voltage applied to the metal needle electrodes 7, so that an increase in the produced amount of ozone due to an increase in the discharge current flowing at the time of discharge increases, can be prevented.

In addition, because a ceaseless measurement of increase and decrease in current leads to monitoring the pollution degree of electrodes, the maintenance timing of the metal needle electrodes 7 can be easily recognized.

Furthermore, if an abnormal current should flow, application of a high voltage to the metal needle electrodes 7 can be stopped and the occurrence of a fire or other dangers can be prevented in advance.

Accordingly, the concentration of ozone in the ozone-contained ionized gas 10 to be supplied to objects 14 on which microorganisms multiply becomes easy to control and moreover the concentration of ozone can be kept low, whose high value becomes harmful, so that the multiplication of microorganisms can be prevented safely and efficiently.

Embodiment 11

Figure 13:
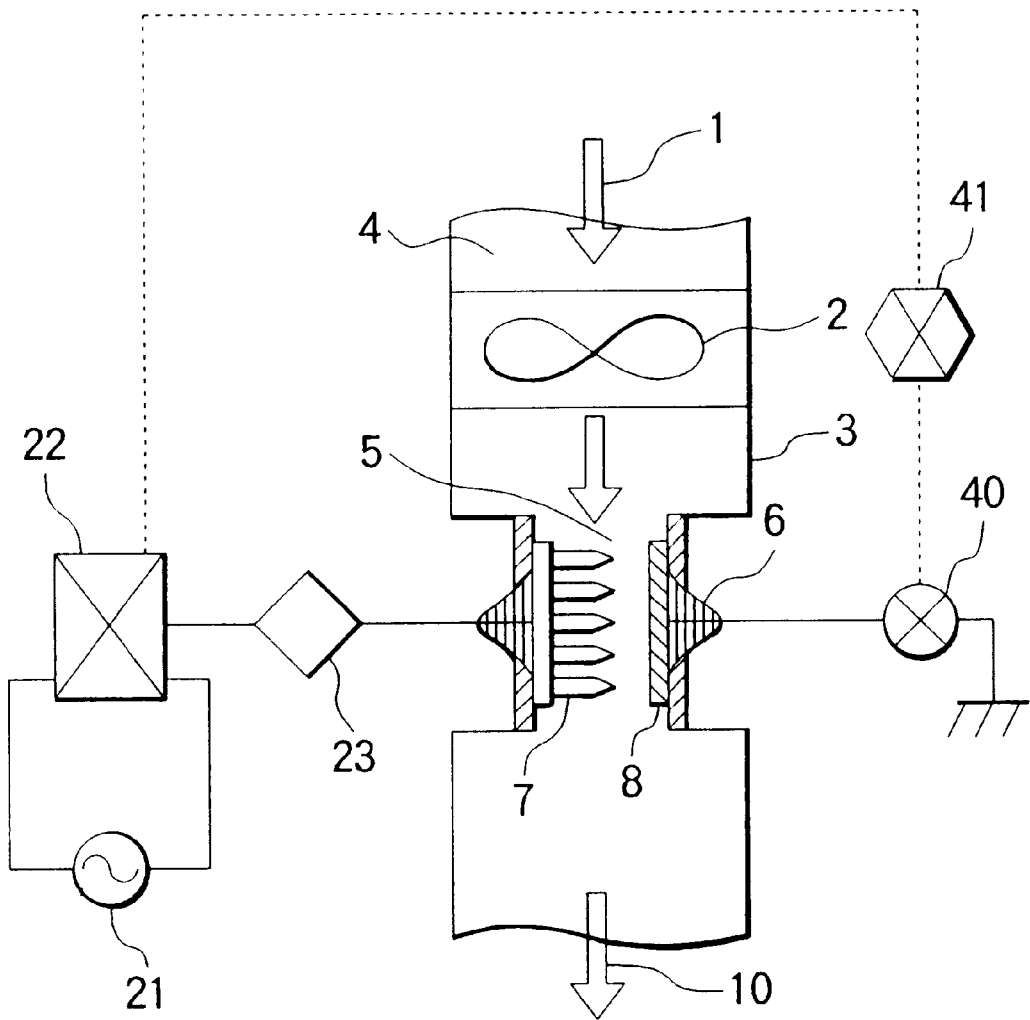
FIG. 13 is a structural drawing showing a microorganism multiplication preventing apparatus according to the embodiment 11 of the present invention.
Figure 14:
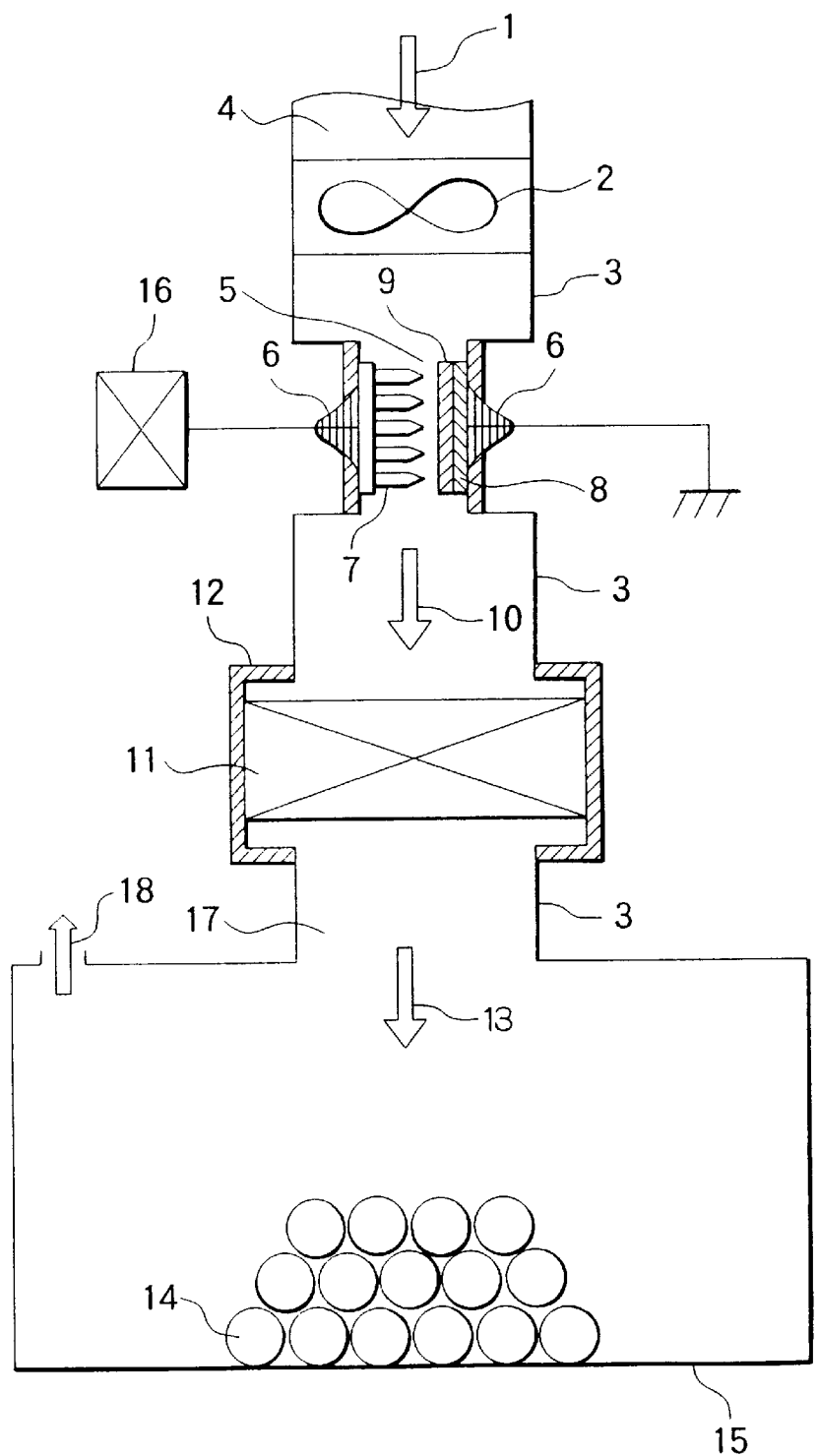
FIG. 14 is a structural drawing showing a conventional microorganism multiplication preventing apparatus.

With the above embodiment 10, there was shown an arrangement in which the concentration of ozone in the gas 1 is kept constant by measuring a value of current flowing into the metal needle electrodes 7, transmitting a signal from the ammeter 40 via the control device 4 to the boosting converter 22 and decreasing the voltage applied to the metal needle electrodes 7, but a similar effect is obtained also with an arrangement in which, with an ammeter 40 provided between the metal plate ground electrode 8 and the ground, the discharge current flowing between both electrodes 7 and 8 is arranged to be measured as shown in the structural drawing of FIG. 13.

In addition, since the ammeter is provided at the portion to which no high voltage is applied, the specification of the ammeter 40 is not required to be a high-voltage one, so that there is an advantage of saving the apparatus cost.

What is claimed is:

1. A microorganism multiplication preventing method, comprising the steps of:

generating a gas containing a concentration of ozone of 0.1 ppm or below and a concentration of ions of at least about $10^4$ ions/cm$^3$, under action of a discharge;

maintaining said concentration of ozone by discharge current control means connected to said electrodes for controlling current flowing at the time of said discharge; and introducing said gas into a space which houses objects to be treated by said gas, thereby preventing the multiplication of microorganisms on said objects and in said space.

2. A microorganism multiplication preventing method, comprising the steps of:

generating a gas containing a concentration of ozone of 0.1 ppm or below and a concentration of ions of at least about $10^4$ ions/cm$^3$, under action of a discharge;

maintaining said concentration of ozone by discharge current control means connected to said electrodes for controlling current flowing at the time of said discharge;

introducing said gas into a space which houses objects to be treated by said gas; and diffusing said gas on said objects in such as manner as to prevent multiplication of microorganisms.

3. A microorganism multiplication preventing apparatus, comprising:

an activated-particle generating chamber;

activated-particle generating electrodes placed in said activated-particle generating chamber for generating a gas containing a concentration of ozone of 0.1 ppm or below in said activated particle chamber under action of a discharge caused by application of a voltage; and discharge current control means connected to said electrodes for reducing the current flowing at the time of said discharge to maintain said concentration of ozone.

4. A microorganism multiplication preventing apparatus as set forth in claim 3, wherein said discharge current control means is a pulse generator for applying a voltage to the activated-particle generating electrode intermittently.

5. A microorganism multiplication preventing apparatus as set forth in claim 3, comprising:

discharge current measuring means for measuring the current flowing at the time of discharge.

6. A microorganism multiplication preventing apparatus as set forth in claim 3, further comprising:

ozone concentration regulating means for regulating an ozone concentration in the gas inside said activated-particle generating chamber.

7. A microorganism multiplication preventing apparatus comprising:

an activated-particle generating chamber;

activated-particle generating electrodes placed in said activated particle generating chamber for generating a gas containing a concentration of ozone of 0.1 ppm or below and a concentration of ions of at least about $10^4$ ions/cm$^3$, in said activated particle generating chamber under action of a discharge caused by application of a voltage; and gas flow control means provided on an upstream side of said activated-particle generating chamber for restricting gas flow as the gas passes through the gas flow control means and attendantly accelerating a flow speed of said gas, and leading said gas to a discharge electrode of said activated-particle generating electrodes and into the gap between the electrodes, and moreover, regulating the flow speed of said gas.

8. A microorganism multiplication preventing apparatus as set forth in claim 7, further comprising:

ozone concentration regulating means for regulating an ozone concentration in the gas inside said activated-particle generating chamber.

9. A microorganism multiplication preventing method, comprising:

generating a gas containing a concentration of ozone of 0.1 ppm or below and a concentration of ions of at least about $10^4$ ions/cm$^3$, under action of a discharge in a space which houses objects to be treated;

maintaining said concentration of ozone within an activated-particle generation chamber, thereby preventing multiplication of microorganisms on said objects and in said space.

10. A microorganism multiplication preventing method according to claim 9, wherein the concentration of ozone is in the range not less than 0.002 ppm and not greater than 0.1 ppm.

* * * * *